United States Patent [19]
Kalvinsh et al.

[11] Patent Number: 5,965,615
[45] Date of Patent: Oct. 12, 1999

[54] HYDROXYL RADICAL SCAVENGER

[75] Inventors: Ivars Kalvinsh, Salaspils; Maris Veveris, Vējabas, both of Latvia; Yasushi Abiko, Asahikawa; Kiyotaka Tajima, Tokushima, both of Japan

[73] Assignees: Taiho Pharmaceutical Co., Ltd., Tokyo, Japan; Valsts zinatniska iestade - bezpelnas organizacija Latvijas organiskas sintezes instituts, Riga, Lithuania

[21] Appl. No.: 08/809,618
[22] PCT Filed: Jul. 23, 1996
[86] PCT No.: PCT/JP96/02057
  § 371 Date: Mar. 25, 1997
  § 102(e) Date: Mar. 25, 1997
[87] PCT Pub. No.: WO97/04767
  PCT Pub. Date: Feb. 13, 1997

[30] Foreign Application Priority Data

Jul. 25, 1995 [JP] Japan ................................ 7-188909

[51] Int. Cl.$^6$ ................................................. A61K 31/205
[52] U.S. Cl. ............................................................. 514/556
[58] Field of Search ........................... 514/556; 560/155; 562/553; 564/293

[56] References Cited

U.S. PATENT DOCUMENTS

| | | | |
|---|---|---|---|
| 4,382,092 | 5/1983 | Carvazza | 424/316 |
| 4,703,045 | 10/1987 | Guinot | 514/159 |
| 5,030,458 | 7/1991 | Shug et al. | 426/2 |

FOREIGN PATENT DOCUMENTS

| | | |
|---|---|---|
| 0244370 | 11/1987 | European Pat. Off. . |
| 59-222412 | 12/1984 | Japan . |
| 2-142759 | 5/1990 | Japan . |
| 3-115220 | 5/1991 | Japan . |

OTHER PUBLICATIONS

Phytochemistry, vol. 28, No. 4 (1989) Sminoff Nicholas, et al., "Hydroxyl radical scavenging activity of compatible solutes", p. 1057, abstract; p. 1058, Table 1.

J.R. Freidel, et al., In vitro Effect of D–Isoascorbic Acid and Betaine Hydrate Alone and in Combination on Normal and Malignant Cells, Expl. Cell Biol. vol. 47, No. 6, 1979, pp. 463–469.

Derwent Publication Ltd., London, GB; Class B04, AN 86–128209; XP002064158 & JP 61065850 A (Kokusai Shiyaku KK), abstract, (1986).

Derwent Publications Ltd., London, GB; Class B04, AN 89–320498; XP002064159 & JP 01238538 A (Toa Yakuhin Kogyo KK), abstract, (1989).

*Primary Examiner*—Phyllis G. Spivack
*Attorney, Agent, or Firm*—Sughrue, Mion, Zinn, Macpeak & Seas, PLLC

[57] ABSTRACT

The invention relates to a hydroxyl radical scavenger and a remedy composition for a disease caused by a hydroxyl radical, which each comprise, as an active ingredient, a betaine represented by the formula (1):

$$(CH_3)_3N^+(CH_2)_nCOO^- \qquad (1)$$

wherein n is an integer of 1–5, or an acid-addition salt or ester salt thereof. The betaine is useful in treating a disease caused by a hydroxyl radical, in particular, cardiopathy.

4 Claims, No Drawings

HYDROXYL RADICAL SCAVENGER

TECHNICAL FIELD

The present invention relates to a hydroxyl radical scavenger having an excellent hydroxyl radical-scavenging action and a remedy composition for a disease caused by a hydroxyl radical.

BACKGROUND ART

There have recently been many clinical reports that active oxygen and free radicals do damage to the membrane tissue of a living body, and this damage participates in the cause of various diseases such as cardiopathy, inflammation, cancer and ischemic disorder.

Active oxygen in vivo includes a superoxide radical ($O_2^-$), hydrogen peroxide ($H_2O_2$), a hydroxyl radical (.OH) and singlet oxygen ($^1O_2$) in an excited state.

As mechanisms for scavenging the active oxygen in vivo, it is considered that the superoxide radical ($O_2^-$) and hydrogen peroxide ($H_2O_2$), which have a relatively long life, are scavenged by enzymes, and the other active oxygen, which has a short life, is scavenged by low-molecular weight compounds such as ascorbic acid. For example, a superoxide radical ($O_2^-$) formed in an erythrocyte is almost all scavenged by superoxide dismutase (SOD), hydrogen peroxide ($H_2O_2$) is scavenged by catalase and peroxidase, and singlet oxygen ($^1O_2$) is scavenged by β-carotene and tocopherol.

However, there has not been yet developed any low-molecular weight compound capable of directly scavenging a hydroxyl radical which is considered to have high reactivity and also be the greatest in organism-damaging action among the active oxygen. Further, it is considered that since the hydroxyl radical reacts to cell components at a rate almost near a diffusion controlled rate, its life is short, so that the organism itself cannot have a special mechanism capable of scavenging this radical.

The formation of the hydroxyl radical in vivo is considered to be caused by the reaction of hydrogen peroxide ($H_2O_2$) with the superoxide radical ($O_2^-$) as represented by the following reaction formula:

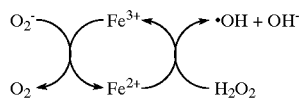

Namely, when an respiratory substrate is oxidized in a mitochondrion of a cytoplasm, the electron of the substrate is transferred to an electron transport system in the exact order, and finally transferred to an oxygen molecule ($O_2$) by cytochrome oxidase to form water ($H_2O$). The $O_2$ molecule in the mitochondrion is reduced by 4 electrons to cleave the $O_2$ molecule into two $H_2O$ molecules. The mechanism of this catalytic action is not yet completely elucidated. However, a reaction easy to occur is the formation of $H_2O_2$ by reduction of $O_2$ with 2 electrons. $H_2O_2$ is reacted with $O_2^-$ to form .OH, a sort of active oxygen high in reactivity. On the other hand, various investigations as to SOD or SOD-like active substances, which catalyze the disproportionation of a superoxide radical ($O_2^-$), have been carried out. However, such catalytic substances involve a problem from the viewpoint of stability, and do not directly scavenge the hydroxyl radical. As scavengers capable of directly scavenging the hydroxyl radical, there have been known a hydroxyl radical scavenger comprising nicorandil as an active ingredient as described in Japanese Patent Application Laid-Open No. 101621/1991, an active oxygen scavenger comprising sesamin or the like as an active ingredient as described in Japanese Patent Application Laid-Open No. 227977/1994, and the like. However, no one has yet succeeded in making their products. As a model for a myocardial damage by a hydroxyl radical, there is a model of cardiac functional and myocardial metabolic disorder induced by the perfusion of $H_2O_2$ using the heart enucleated from a rat (Am. J. Physiol., Vol. 265, No. 5, H1478–1485 (1993)). In this model, it has been reported that lidocaine having antiarrhythmic action and membrane-stabilizing action exhibits an improving effect in a concentration of 50–200 μM.

Accordingly, it is an object of the present invention to provide a substance having a directly scavenging action on a hydroxyl radical and a medicine composition capable of treating various diseases by such an action.

DISCLOSURE OF THE INVENTION

The present inventors have carried out an extensive investigation as to the hydroxyl radical-scavenging actions of various low-molecular weight compounds. As a result, it has been found that betaines, particularly, betaines represented by the following general formula (1), and acid-added salts and ester salts thereof have an extremely good hydroxyl radical-scavenging action, and are hence useful as hydroxyl radical scavengers and remedies for diseases caused by a hydroxyl radical, thus leading to completion of the present invention.

Namely, the present invention is directed to a hydroxyl radical scavenger comprising, as an active ingredient, a betaine represented by the general formula (1):

(1)

wherein n stands for an integer of 1–5, or an acid-addition salt or ester salt thereof.

The present invention is also directed to a remedy composition for a disease caused by a hydroxyl radical, which comprises the betaine (1), or an acid-addition salt or ester salt thereof and a pharmaceutically permissible carrier.

The present invention is further directed to use of the betaine (1), or an acid-addition salt or ester salt thereof for the preparation of a remedy for a disease caused by a hydroxyl radical.

The present invention is still further directed to a method of treating a disease caused by a hydroxyl radical, which comprises administering an effective amount of the betaine (1), or an acid-addition salt or ester salt thereof.

BEST MODE FOR CARRYING OUT THE INVENTION

The betaines represented by the general formula (1) and the ester salts thereof are known compounds described in, for example, Japanese Patent Publication Nos. 33887/1976 and 36732/1976, Japanese Patent Application Laid-Open Nos. 65850/1986 and 190654/1989, etc. In particular, γ-butyrobetaine represented by

has been known as useful as a remedy for L-carnitine deficiency (see Japanese Patent Publication No. 24325/1992), and an antidandruff agent and a hair cosmetic ingredient owing to its peroxylipid-inhibiting action (see Japanese Patent Application Laid-Open No. 275516/1989).

Besides, carpronium chloride, which is the methyl ester chloride thereof, has been known as useful as a hair growth stimulant owing to its local vasodilative action (see Japanese Patent Publication No. 56683/1985), a remedy for various diseases caused by reduction in function of the digestive tract, such as chronic gastritis and gastric atony, owing to its parasympathomimetic action (see Japanese Patent Publication No. 33887/1976), and a remedy for dermatopathy owing to its sebum secretion-facilitating action and sweating-facilitating action (see Japanese Patent Publication No. 30644/1086).

However, the fact that these betaines and ester salts thereof have a hydroxyl radical-scavenging action and are hence useful as hydroxyl radical scavengers has not been known at all.

As the acid-addition salts of the betaines represented by the general formula (1), any salts with inorganic acids or organic acids may be permissible so far as they may be pharmaceutically permissible salts. As examples of the inorganic acids, may be mentioned hydrohalogenic acids such as hydrochloric acid, hydrobromic acid and hydriodic acid, nitric acid, sulfuric acid, tetrafluoroboric acid, perchloric acid, phosphoric acid, and metaphosphoric acid. As examples of the organic acids, may be mentioned organic sulfonic acids such as methanesulfonic acid, toluenesulfonic acid, nitrobenzenesulfonic acid, picrylsulfonic acid, camphorsulfonic acid and 1,5-naphthalenedisulfonic acid, acetic acid, propionic acid, isobutyric acid, fumaric acid, succinic acid, stearic acid, citric acid, lactic acid, maleic acid, oleic acid, malonic acid, benzoic acid, ascorbic acid, glycyrrhetinic acid, and nicotinic acid. Of these acid-added salts, the salts with hydrohalogenic acids and toluenesulfonic acid are preferred with the hydrochlorides being particularly preferred.

As the ester salts of the betaines according to the present invention, may be mentioned those represented by the following general formula (1a):

wherein n has the same meaning as defined above, Y is a protective group for the carboxyl group, and X denotes an acid residue.

In the general formula (1a), no limitation is imposed on the protecting group for the carboxyl group indicated by Y so far as it may be easily separated by a simple chemical treatment (for example, hydrolysis, reduction, acid decomposition, etc.) if desired, or in a living body after administration. Examples thereof include protective groups described in Japanese Patent Publication Nos. 33887/1976 and 36732/1976, Japanese Patent Application Laid-Open Nos. 65850/1986 and 190654/1989, etc. Specific examples thereof include linear or branched lower alkyl groups having 1–6 carbon atoms, such as methyl, ethyl, n-propyl, isopropyl, n-butyl, isobutyl, sec-butyl, tert-butyl, pentyl, isopentyl and hexyl; halogenated lower alkyl groups such as 2-iodoethyl, 2,2-dibromoethyl, 2,2,2-trichloroethyl and 2,2,2-tribromoethyl; aralkyl groups such as benzyl, p-methoxybenzyl, o-nitrobenzyl and p-nitrobenzyl; and aromatic residues, which may have a substituent, such as phenyl, p-nitrophenyl, tolyl and naphthyl. The lower alkyl groups are more preferable protective groups for the carboxyl group with a methyl group being particularly preferred.

No limitation is imposed on the acid residue indicated by X so far as it is pharmaceutically permissible, and it may be either an inorganic acid residue or an organic acid residue.

As examples of the inorganic acid residue, may be mentioned residues of hydrohalogenic acids such as hydrochloric acid, hydrobromic acid and hydriodic acid, and residues of acids such as nitric acid, sulfuric acid, tetrafluoroboric acid, perchloric acid, phosphoric acid and metaphosphoric acid. As examples of the organic acid residue, may be mentioned residues of organic sulfonic acids such as methanesulfonic acid, toluenesulfonic acid, nitrobenzenesulfonic acid, picrylsulfonic acid, camphorsulfonic acid and 1,5-naphthalenedisulfonic acid, and residues of organic acids such as acetic acid, propionic acid, isobutyric acid, fumaric acid, succinic acid, stearic acid, citric acid, lactic acid, maleic acid, oleic acid, malonic acid, benzoic acid, ascorbic acid, glycyrrhetinic acid and nicotinic acid. Of these acid residues, the acid residue of the hydrohalogenic acids and toluenesulfonic acid are preferred with the acid residue of hydrochloric acid being particularly preferred.

Preferable examples of the compounds of the general formula (1) are compounds wherein n is 1–3, such as glycinebetaine, alaninebetaine and γ-butyrobetaine, and acid-addition salts and lower alkyl ester salts thereof. More preferable compounds are γ-butyrobetaine, and the acid-addition salts and thereof with γ-butyrobetaine, the hydrochloride thereof being particularly preferred.

Incidentally, the compounds represented by the general formula (1) in the present invention, and the acid-addition salts and ester salts thereof may be present in the form of hydrates.

The compounds represented by the general formula (1) are prepared in accordance with the known methods described in, for example, Japanese Patent Publication Nos. 33887/1976, 36732/1976 and 45668/1984, Japanese Patent Application Laid-Open No. 65850/1986, Japanese Patent Publication No 66859/1992, and U.S. Pat. No. 4,806,282.

The hydroxyl radical scavenger and remedy composition for diseases caused by a hydroxyl radical according to the present invention (hereinafter may be referred to as "the composition according to the present invention" simply) can be orally or parenterally administered to mammals including the human. No particular limitation is imposed on the dose form of the composition according to the present invention, and a variety of pharmaceutical dose forms may be used as necessary for the end application intended for prevention or treatment. As examples of the dose form, may be mentioned oral preparations, injection preparations, suppository preparations, external preparations (for example, plasters such as poultices, ointments, creams, lotions, and the like), ophthalmic solutions and collunaria.

Examples of the diseases caused by a hydroxyl radical in the present invention include cardiopathy (including cardiac insufficiency, stricture of the heart, hypercardia, ischemic disorder caused by reperfusion, disorder caused after the operation of percutaneous transluminal coronary angioplasty, etc.), cancer, radiation damage, inflammation, rheumatism, cataract, diseases caused by side effects of carcinostatic agents, and renal disorder. The composition according to the present invention is particularly useful as a remedy for the cardiopathy among these diseases.

The composition according to the present invention may be prepared for use by incorporating pharmaceutical carriers or excipients optionally and routinely used into the compound according to the present invention in accordance with the conventional method.

More specifically, when the composition is prepared in the form of tablets, capsules, granules or powder for oral administration, there may be used, as carriers, excipients such as lactose, sucrose, sodium chloride, glucose, urea, starch, calcium carbonate, kaolin, crystalline cellulose and silicic acid; binders such as water, ethanol, propanol, simple syrup, glucose solution, starch solution, gelatin solution, carboxymethylcellulose, hydroxypropylcellulose, hydroxypropylstarch, shellac, methylcellulose, ethylcellulose, calcium phosphate and polyvinyl pyrrolidone; disintegrators such as dry starch, sodium alginate, agar powder, laminaran powder, sodium hydrogencarbonate, calcium carbonate, polyoxyethylene sorbitan fatty acid esters, sodium lauryl sulfate, stearic acid monoglyceride, starch and lactose; disintegration-preventing agents such as sucrose, stearic acid, cacao butter and hydrogenated oils; absorbefacients such as quaternary ammonium bases and sodium lauryl sulfate; humectants such as glycerol and starch; adsorbents such as starch, lactose, kaolin, bentonite and colloidal silica; lubricants such as purified talc, stearic acid salts, boric acid powder and polyethylene glycol; taste corrigents such as sucrose, orange peel, citric acid and succinic acid; and the like. The tablets may be provided as tablets coated with usual coatings, for example, sugar-coated tablets, gelatin-coated tablets, enteric coated tablets, film-coated tablets, double coated tablets, multilayer-coated tablets and the like. The capsules are prepared by mixing the compound according to the present invention with the various carriers exemplified above and charging the mixture into hard gelatin capsules, soft capsules and the like.

A liquid composition for oral administration may be an aqueous or oily suspension, solution, syrup or elixir, and is prepared by suitably adding taste corrigents, buffers, stabilizers, odor corrigents and/or the like to the compound according to the present invention in accordance with a method known per se in the art. In this case, the taste corrigents may be the same as mentioned above. The buffers include sodium citrate and the like, and the stabilizers include tragacanth gum, gum arabic, gelatin and the like.

An injection may be an aqueous or oily suspension or solution, or a powdered or lyophilized preparation to be dissolved at the time it will be used. When the injection is prepared, it is formulated by suitably adding pH adjustors, buffers, stabilizers, isotonicity-imparting agents, diluents, local anesthetics and/or the like to the compound according to the present invention in accordance with a method known per se in the art. In this case, as the pH adjustors and buffers, may be mentioned sodium citrate, sodium acetate, sodium phosphate and the like. As the stabilizers, may be mentioned sodium pyrosulfite, ethylenediaminetetraacetic acid (EDTA), thioglycolic acid, thiolactic acid and the like. Examples of the diluents include water, aqueous solutions of lactic acid, ethyl alcohol, propylene glycol, ethoxylated isostearyl alcohol, polyoxylated isostearyl alcohol and polyoxyethylene sorbitan fatty acid esters. As the stabilizers, may be mentioned sodium pyrosulfite, EDTA, thioglycolic acid, thiolactic acid and the like. As the local anesthetics, may be mentioned procaine hydrochloride, lidocaine hydrochloride and the like.

When the composition is prepared in the form of a suppository, for example, polyethylene glycol, lanolin, cacao butter, esters of higher alcohols, gelatin, semisynthetic glycerides and the like may be used as carriers together with surfactants such as Tween (trade mark) as needed.

When the composition is prepared in the form of an ointment (paste, cream, gel or the like), a base, a stabilizer, a wetting agent, a preservative and the like, which are routinely used, are incorporated as needed. As examples of the base, may be mentioned liquid paraffin, white petrolatum, bleached bees wax, octyldodecyl alcohol and paraffin. As examples of the preservative, may be mentioned methyl p-hydroxybenzoate, ethyl p-hydroxybenzoate and propyl p-hydroxybenzoate.

When the composition is prepared in the form of a plaster, it is only necessary to apply the above ointment, cream, gel or paste to a support routinely used in accordance with a method known per se in the art. As the support, a fabric or nonwoven fabric made of cotton, staple fibers or chemical fibers, or a film or foamed sheet of non-rigid polyvinyl chloride, polyethylene or polyurethane is suitable.

In the above individual compositions, may be further incorporated colorants, preservatives, perfume bases, flavors, edulcorants, and other drugs, for example, carcinostatic agents, antiphlogistics and remedies for cardiopathy, as needed.

No particular limitation is imposed on the administration method of the compositions according to the present invention, and it may suitably be determined according to its preparation form, the age, sex and other conditions of a patient to be dosed, the diseased condition of the patient, and the like. For example, the tablets, pills, powder, solution, suspension, emulsion, granules and capsules are orally dosed. The suppository is intrarectally dosed. The injection is intraarterially dosed by themselves or in combination with a usual fluid replacement containing glucose, amino acids and/or the like, and further intravenously, intramuscularly, intracutaneously, subcutaneously or intraperitoneally dosed by themselves as needed. The ointment is applied to the skin, oral mucosa membrane, etc. The plaster is applied to the skin. The collunarium is administered in the nasal cavity, and the ophthalmic solution is topically administered to eyes.

The dose of the active ingredient in each of the compositions according to the present invention may suitably be selected according to an administration method, the age, sex and other conditions of a patient to be dosed, the diseased condition of the patient, and the like. In general, the dose per day of the active ingredient is however within a range of 1–1,000 mg/kg of weight/day, preferably 5–300 mg/kg of weight/day. These compositions according to the present invention may be dosed at once or in about 2–4 installments a day.

EXAMPLES

The present invention will hereinafter be described in detail by the following examples. However, the present invention is not limited to and by these examples.

Test Example: (Improving Test of Myocardial Metabolic Disorder Caused by a Hydroxyl Radical)

1. Drug to be Used

γ-Butyrobetaine hydrochloride (product of Aldrich Chemical Co., Inc.) was used as a test compound.

2. Experimental Method and Result

An experiment was performed with reference to the method described in "American Journal of Physiology", Vol. 265, No. 5, H1478–1485 (1993). More specifically, the heart of a rat aged 9–10 weeks was enucleated and perfused with a Krebs-Henseleit hydrogencarbonate buffer (118 mM NaCl, 4.7 mM KCl, 1.2 mM $KH_2PO_4$, 1.2 mM $MgSO_4$, 2.5 mM $CaCl_2$, 25 mM $NaHCO_3$, 11 mM glucose) saturated by a gaseous mixture containing 95% of $O_2$ and 5% of $CO_2$ at 37° C. in accordance with the Langendorff's method. This process was carried out by first perfusing for 10 minutes under a fixed pressure of 80 cm $H_2O$ and then perfusing at a fixed flow rate of 10 ml/min using a microtube pump. The heart rate was paced at 300 times/min by means of an electric stimulator to keep it constant during the experiment. As an index to a cardiac function, left-ventricular systolic and diastolic pressures were measured to calculate a pressure produced in a left ventricle in accordance with the following equation.

$$\text{Pressure produced in the left venticle} = \text{Left-ventricular systolic pressure} - \text{Left-ventricular diastolic pressure}$$

As an index to energy metabolism, a content of adenosine triphosphate (ATP) in the cardiac muscle was measured after completion of the experiment.

As a control group, 600 μM aqueous hydrogen peroxide was administered for 3 minutes upon elapsed time of 2 minutes after the perfusion with the buffer, thereby measuring the pressure produced in the left ventricle and the ATP content in the cardiac muscle. By this process, it was observed that the pressure produced in the left ventricle is continuously reduced and the ATP content in the cardiac muscle is lowered, both, due to the production of a hydroxyl radical.

Next, 600 μM aqueous hydrogen peroxide was administered for 3 minutes upon elapsed time of 2 minutes after the perfusion with the buffer containing the compound to be tested, thereby measuring the same parameters. The results are shown in Table 1.

TABLE 1

| Compound | Concentration (mM) | Pressure produced in left ventricle (mmHg) | ATP content (μM) |
|---|---|---|---|
| Control group | — | <5 | 7 |
| γ-Butyrobetaine | 0.5 | 10 | 10.5 |
|  | 1.0 | 25 | 12 |

As apparent from the above results, γ-butyrobetaine significantly improved the reduction in the pressure produced in the left ventricle due to the hydroxyl radical and exhibited an ATP content-increasing effect to significantly improve myocardial metabolic disorder.

Preparation Example 1: Tablet Preparation

| Glycinebetaine hydrochloride | 100 mg |
|---|---|
| Microcrystalline cellulose | 50 mg |
| Hydroxypropylcellulose | 20 mg |
| Lactose | 47 mg |
| Talc | 2 mg |
| Magnesium stearate | 1 mg |

A tablet preparation containing the ingredients in a proportion of 220 mg/tablet was formulated in accordance with the above formulation and a method known per se in the art.

Preparation Example 2: Granule Preparation

| Alaninebetaine hydrochloride | 200 mg |
|---|---|
| Lactose | 400 mg |
| Corn starch | 370 mg |
| Hydroxypropylmethylcellulose | 30 mg |

A granule preparation containing the ingredients in a proportion of 1000 mg/wrapper was formulated in accordance with the above formulation and a method known per se in the art.

Preparation Example 3: Capsule Preparation

| γ-Butyrobetaine hydrochloride | 50 mg |
|---|---|
| Lactose | 50 mg |
| Corn starch | 50 mg |
| Microcrystalline cellulose | 94 mg |
| Magnesium stearate | 1 mg |

A capsule preparation containing the ingredients in a proportion of 245 mg/capsule was formulated in accordance with the above formulation and a method known Per se in the art.

Preparation Example 4: Injection Preparation

| Carpronium chloride | 70 mg |
|---|---|
| Sodium chloride | 3 mg |
| Water for injection | q.s. |
|  | One ampule contained 2 ml. |

An injection preparation was formulated in accordance with the above formulation and a method known per se in the art.

Preparation Example 5: Syrup Preparation

| γ-Butyrobetaine hydrochloride | 500 mg |
|---|---|
| Purified sucrose | 60 mg |
| Ethyl p-hydroxybenzoate | 5 mg |
| Butyl p-hydroxybenzoate | 5 mg |
| Perfume base | q.s. |
| Colorant | q.s. |
| Purified water | q.s. |

A syrup preparation in an amount of 100 ml was formulated in accordance with the above formulation and a method known Per se in the art.

Preparation Example 6: Suppository Preparation

| Carpronium chloride | 100 mg |
|---|---|
| Witepsol W-35 (trade mark; mixture of mono-, di- and triglycerides of saturated fatty acids from lauric acid to stearic acid; product of Dynamit Nobel Co.) | 1400 mg |

A suppository preparation containing the ingredients in a proportion of 1,500 mg/suppository was formulated in accordance with the above formulation and a method known per se in the art.

Industrial Applicability

The hydroxyl radical scavengers according to the present invention have an excellent hydroxyl radical-scavenging action and are hence useful in treating diseases caused by a hydroxyl radical, in particular, cardiopathy.

We claim:

1. A method of treating a disease caused by a hydroxyl radical, which comprises administering a therapeutically effective amount of a betaine represented by formula (1):

$$(CH_3)_3N^+(CH_2)_nCOO^- \qquad (1)$$

wherein n stands for an integer of 1–5, or an acid-addition salt or ester salt thereof.

2. The treating method according to claim 1, wherein the betaine is a compound in which n in formula (1) is an integer of 1–3, or an acid-addition salt or lower alkyl ester salt thereof.

3. The treating method according to claim 1, wherein the betaine is γ-butyrobetaine or an acid-addition salt thereof.

4. The treating method according to claim 1, wherein the disease caused by hydroxyl radical is cardiopathy.